US006911561B2

(12) United States Patent
Krasutsky et al.

(10) Patent No.: US 6,911,561 B2
(45) Date of Patent: Jun. 28, 2005

(54) COMPOSITIONS INCLUDING FLUORINATED PEROXIDES, METHODS OF MAKING, AND THE USE THEREOF

(75) Inventors: Pavel A. Krasutsky, Duluth, MN (US); Robert M. Carlson, Duluth, MN (US); Igor V. Kolomitsyn, Duluth, MN (US); Hong Wang, Harleysville, PA (US)

(73) Assignee: Regents of the University of Minnesota, Minneapolis, MN (US)

( * ) Notice: Subject to any disclaimer, the term of this patent is extended or adjusted under 35 U.S.C. 154(b) by 166 days.

(21) Appl. No.: 10/163,840

(22) Filed: Jun. 5, 2002

(65) Prior Publication Data

US 2003/0004369 A1 Jan. 2, 2003

Related U.S. Application Data
(60) Provisional application No. 60/294,820, filed on Jun. 5, 2001.

(51) Int. Cl.[7] .............................................. C07C 409/00
(52) U.S. Cl. ...................................... 568/566; 568/558
(58) Field of Search ................................ 568/558, 566; 502/300, 301, 344

(56) References Cited

U.S. PATENT DOCUMENTS

| 2,559,630 A | 7/1951 | Bullitt, Jr. et al. |
| 2,580,358 A | 12/1951 | Miller et al. |
| 2,580,373 A | 12/1951 | Zimmerman |
| 2,700,662 A | 1/1955 | Young et al. |
| 2,775,618 A | 12/1956 | Dittman et al. |
| 2,792,423 A | 5/1957 | Young et al. |
| 2,943,080 A | 6/1960 | Bro |
| 3,079,443 A | * 2/1963 | Barrett et al. ............... 568/566 |
| 3,461,155 A | 8/1969 | Rice |
| 5,068,454 A | 11/1991 | Sawada et al. |

FOREIGN PATENT DOCUMENTS

| DE | 1806426 | 5/1969 |
| GB | 781532 | 8/1957 |
| GB | 794830 | 5/1958 |
| JP | 1-197467 | 8/1989 |
| JP | 1-249752 | 10/1989 |
| WO | WO 97/08142 | 3/1997 |
| WO | WO01/17939 | 8/2000 |
| WO | WO 01/17939 A1 | 3/2001 |

OTHER PUBLICATIONS

CA:99:142435 abs of DE3203063 Aug. 1983.*
Acession number from Chemical abstracts 2003:431764 CN 1360848 Jul. 2002.*
Bartlett et al., "A Series of Tertiary Butyl Peresters Showing Concerted Decomposition," *J. Am. Chem. Soc.*, Mar. 20, 1958; 80:1398–1405.
Burdon et al., "Aromatic Polyfluoro–compounds. Part XLIV.[1] Bis(pentafluorobenzoyl) Peroxide," *J. Chem. Soc. (C)*, 1969; 5:822–3.

Emmons, "Peroxytrifluoroacetic Acid II. The Oxidation of Anilines to Nitrobenzenes[1]," *J. Am. Chem. Soc.*, Jul. 5, 1954; 76:3470–2.
Fehr, "Diastereoface–Selective Epoxidations: Dependency on the Reagent Electrophilicity," *Angew. Chem. Int. Ed.*, 1998; 37(17):2407–9.
Gumprecht et al., "A Novel Telomerization* Procedure for Controlled Introduction of Perfluoro–n–Alkyl End Groups," *J. Fluorine Chem.*, Mar. 1975; 5(3):245–63.
Hayakawa et al., "Gas and vapor permeability of perfluroalkylated polymers," *Polym. Bull.*, 1994; 32(5/6):661–8.
Hjelmeland et al., "The Electronic Structure of Peracids. Functional Models for Cytochrome P–450," *Tetrahedron*, 1977; 33(9):1029–36.
Jensen et al., "Diastereoselective Peracid Epoxidation: Control of the Face Selectivity via Functional Group Tuning and Proper Choice of Epoxidation Reagent," *Tetrahedron Lett.*, May 14, 1998; 39(20):3213–4.
Kasai, "Perfluoropolyethers with Acid End Groups: An ESR Study of Decarboxylation," *Chem. Mater.*, 1994; 6:1581–6.
Kobayashi et al., "Trifluromethylation of Aromatic Compounds," *Tetrahedron Letters*, 1969; 47:4095–6.
Kopitzky et al., "Bix(trifluoroacetyl) Peroxide, $CF_3C(O)OOC(O)CF_3$," *Inorg. Chem.*, 2001; 40:2693–8.
Krasutsky et al., "New Catalytic Pathway for Bistribluoroacylperoxide Generation." Posters presented at the Aug. 28, 2001 Chicago meeting of the American Chemical Society.
Barlett et al., "t–Butylperoxyesters of *exo–* and *endo–*2–Norbornanecarboxylic Acids," *J. Am. Chem. Soc.*, Jun. 20, 1962; 84:2445–7.
Kratsutsky et al., "New catalytic pathway to bistribluoroacylperoxide generation," available on–line Jun., 2001, [retrieved Aug. 28, 2002]. Retrieved from the Internet: <URL: http://chemistry.org/portal/PersonalSchedule/EventView.jsp?paper_key=192088& session_key=33572>.
Krasutsky et al., "A Novel Pathway for Carbocation Generation through Decomposition of Acyltrifluoracetylperoxides." Posters presented at the Aug. 28, 2001 Chicago meeting of the American Chemical Society.
Krasutsky et al., "Novel pathway for carbocation generation through decomposition of acyltrifluoracetylperoxides," available on–line Jun., 2001, [retrieved Aug. 28, 2002]. Retrieved from the Internet <URL: http://chemistry.org/portal/PersonalSchedule/EventView.jsp?paper_key=192089 &session_key=33572>.
Krasutsky et al., "A Novel Catalytic Pathway for Perfluroacyl Peroxide Synthesis," *Organic Letters*, 2001; 3(19):2997–99.

(Continued)

*Primary Examiner*—Jean F. Vollano
(74) *Attorney, Agent, or Firm*—Mueting, Raasch & Gebhardt, P.A.

(57) ABSTRACT

Methods of making compositions including fluorinated peroxides are disclosed. The compositions are useful, for example, for reacting with organic compounds. In one embodiment, novel peroxides are provided.

23 Claims, 1 Drawing Sheet

OTHER PUBLICATIONS

Krasutsky et al., "A Consecutive Double–Criegee Rearrangement Using TFPAA: Stepwise Conversion of Homoadamantane to Oxahomoadamatanes," *J. Org. Chem.,* Mar. 9, 2001; 66(5):1701–7.

Krasutsky et al., "Observation of a Stable Carbocation in a Consecutive Criegee Rearrangement with Trifluroperacetic Acid," *J. Org. Chemistry,* 2000; 65(13):3926–33.

Krasutskii et al., "Oxidative Fragmentation of Saturated Hydrocarbons. II.* Oxidative Fragmentation of 1,3,5–Trimethyladamantane**," *Russian J. Org. Chem.,* 1996; 32(7):985–989.

Krasutsky et al., "A New One–Step Method for Oxaadamantane Synthesis," *Tetrahedron Lett.,* Aug. 5, 1996; 37(32):5673–4.

Krasutskii et al., "Oxidative Fragmentation of Saturated Hydrocarbons. I. A New Oxidative Fragmentation in the Adamantane Series—A Path to the Synthesis of 1,3,5–Al-l–Cis Derivatives of Cyclohexane," *Russian J. Org. Chem.,* Aug. 10, 1994; 30(3):396–400.

Matsui et al., "Perfluoroalkylquinones. Synthesis Using Bis(perfluoroalkanoyl) Peroxides, Absorption Bands, and Solubility," *Bull. Chem. Soc. Jpn.,* 1995; 68: 1042–51.

Noftle et al., "Preparation and Properties of Bis(trifluoromethylsulfuryl) Peroxide and Trifluoromethyl Trifluoromethanesulfonate," *Inorganic Chemistry,* Jul., 1965; 4(7):1010–12.

Ogino et al., "Syntheses and Properties of Sodium Fluoroalkylbenzenesulfonates," *J. Jpn. Soc. Colour Chem.,* 1992; 65:205–11. English language abstract.

Pandiarajan, "Chapter 2: Hydrogen Peroxide," *Synthetic Reagents,* Pizey, ed., West Sussex, England, 1985; 6:737–750, title page, table of contents.

Renz et al., "100 Years of Baeyer—Villiger Oxidations," *Eur. J. Org. Chem.,* Apr., 1999; 737–50.

Price et al., "p–Nitrobenzoyl Peroxide [Peroxide, bis(p–nitrobenzoyl)]", Shriner and Tilford eds., *Organic Syntheses,* New York, New York, 1955; Collective Vol. 3: 649–50.

Rice et al., "Functionally–Terminated Copolymers of Vinyldene Fluoride and Hexafluropropene," *Am. Chem. Soc., Div. Polym. Sci.,* Mar., 1971; 12(1):396–402.

Sawada, "Chemistry of fluoroalkanoyl peroxides, 1980–1988," *J. Fluorine Chem.,* 2000; 105:219–20.

Sawada et al., "Direct aromatic fluoroalkylations of poly(p–phenylene) with fluoroalkanoyl peroxides: an approach to highly soluble fluorinated conducting polymers," *J. Fluorine Chem.,* 1997; 82:51–4.

Sawada, "Fluorinated Peroxides," *Chem. Rev.,* Jul.–Aug., 1996; 96(5):1779–1808.

Sawada et al., "Perfluoropropylated Phenol and Aniline Derivatives with Perfluorobutyryl Peroxide," *J. Jpn. Res. Institute Mater Technol.,* 1994; 12(64):185–191, with English abstract.

Sawada, "Synthesis of perfluoro–oxa–alkylated compounds by the use of perfluoro–oxa–alkanoyl peroxides and their applications." *J. Fluorine Chem.,* 1993; 61:253–72.

Sawada, "Fluorinated Organic Peroxides—Their Decomposition Behavior and Applications," *Reviews on Heteroatom Chemistry,* 1993; 8:205–31.

Sawada et al., "Trifluoromethylation of Aromatic Compounds with Bis(Trifluoracetyl) Peroxide," *J. Fluorine Chemistry,* Mar., 1990; 46(3):423–31.

Sawada et al., "MNDO MO Theoretical Study of Electronic Structure and Homolytic Dissociation of Perfluoroalkanoyl Peroxides," *J. Fluorine Chem.,* Dec., 1990; 50(3):393–410.

Sawada et al., "Perfluoropropylation of Furans, Thiophenes, and Pyridines with Bis(heptafluorobutyryl) Peroxide," *Bull. Chem. Soc. Jpn.,* 1986; 59(1):215–9.

Sawada et al., "Organic Syntheses with Organic Peroxides: Utilization to Fluoroalkylating Reagents," *Journal of the Japan Oil Chemists' Society,* 1989; 38(1):32–46. English language abstract.

Silbert et al., "Peroxides. VI.[2] Preparation of t–Butyl Peresters and Diacyl Peroxides of Aliphatic Monobasic Acids[3]," *J. Am. Chem. Soc.,* May 20, 1959; 81:2364–7.

Swern, "Chapter VII: Methods of Preparation and Analysis of Organic Peroxy Acids," *Org. Peroxides,* Swern, ed., New York, NY, 1970; 1:475–516.

Yoshida et al., "Heptofluoropropylation of Electron–Rich Olefins with Bis(heptafluorobutyryl) Peroxide," *Chem. Letters,* 1985; 1:755–8.

Yoshida et al., "Perfluoropropylation of Aromatic Coumpounds with Bix(heptafluorofutyryl) Peroxide," *J. Chem. Soc. Chem. Commun.,* 1985; 1:234–6.

Yoshida et al., "Perfluoroalkylations of Nitrogen–containing Heteroaromatic Compounds with Bis(perfluoroalkanoyl) Peroxides," *J. Chem. Soc. Perkin Trans. 1,* May, 1989; 5:909–89.

Yoshida et al., "Reaction of $C_{60}$ with Diacyl Peroxides Containing Perfluoroalkyl Groups. The First Example of Electron Transfer Reaction via $C_{60}+$ in Solution," *Tetrahedron Letters,* 1993; 37(47):7629–32.

Yoshida et al., "Recent progress in Perfluroalkylation by Radical Species with Special Reference to the Use of Bis(perfluoroalkanoyl) Peroxides," *J. Fluorine Chem.,* 1990; 49:1–20.

Zhao et al., "Thermal Decomposition of Some Perfluoro–Polyfluorodiacyl Peroxides," *J. Org. Chemistry,* 1982; 47:2009–13.

Emmons, "Peroxytrifluoroacetic Acid. I. The Oxidation of Nirtosamines to Nitramines," *J. Am. Chem. Soc.,* Jul. 1954;76:3468–3470.

Emmons et al., "Peroxytrifluoroacetic Acid. III. The Hydroxylation of Olefins," *J. Am. Chem. Soc.,* Jul. 1954;76:3472–3474.

Emmons et al., "Peroxytrifluoroacetic Acid. IV. The Epoxidation of Olefins," *J. Am. Chem. Soc.,* Jan. 1955;77:89–92.

Webster's New Collegiate Dictionary, G. & C. Merriam Co., 1979;172 pg.

Hudlicky, "Development of Chemistry of Organic Compounds of Fluorine," *Chemistry of Organic Fluorine Compounds,* Chicester, Sussex, England, 1976, cover page, title page, table of contents, and pp. 1–6.

* cited by examiner

Figure 1.

COMPOSITIONS INCLUDING FLUORINATED PEROXIDES, METHODS OF MAKING, AND THE USE THEREOF

CROSS-REFERENCE TO RELATED APPLICATIONS

The present application claims priority to U.S. patent application Ser. No. 60/294,820, filed on Jun. 5, 2001, which is incorporated herein by reference.

BACKGROUND

Fluorinated peroxides have been reported to be useful in a variety of areas of organic synthesis. Fluorinated peroxides manifest unique properties, which are attractive not just for fundamental, but also for applied chemistry. For example, this class of peroxides can be used as active radical initiators for the polymerization of halogenated olefins and as reagents for perfluoroalkylation of polymers and monomers. It has been reported that even polymeric hydrocarbon materials can be perfluorinated with fluorinated peroxides.

Fluorinated peroxides have commonly been prepared by the reaction of perfluoroacyl chlorides or anhydrides with hydrogen peroxide under basic aqueous conditions. This method suffers from the hydrolysis and loss of starting reagents (e.g., perfluoroacyl chlorides and/or anhydrides) as well as loss of hydrolyzable products (e.g., bis(perfluoroacyl) peroxides). The formation of salt by-products in this method is also undesirable.

Numerous attempts have been devoted to developing improved methods for preparing fluorinated peroxides. Despite the attempts, convenient methods for preparing fluorinated peroxides for laboratory and/or industrial applications are desired in the art.

SUMMARY OF THE INVENTION

The present invention provides methods of preparing fluorinated peroxides that are generally more desirable than conventional methods.

In one embodiment, there is provided a method of making a composition that includes a perfluorinated peroxide of the formula $R_fC(O)OOC(O)R_f$. The method includes combining a perfluorinated anhydride of the formula $R_fC(O)OC(O)R_f$ with hydrogen peroxide and a catalytic amount of a salt, a metal oxide, a metal hydroxide, a metal alcoholate, or a combination thereof.

In another embodiment, there is provided a method of making a composition that includes a perfluorinated peroxide of the formula $R_fC(O)OOC(O)R_f$. The method includes combining a perfluorinated anhydride of the formula $R_fC(O)OC(O)R_f$ with hydrogen peroxide and a non-carbonate salt, a metal oxide, a metal hydroxide, a metal alcoholate, or a combination thereof.

In yet another embodiment, there is provided a method of making a non-aqueous composition that includes a perfluorinated peroxide of the formula $R_fC(O)OOC(O)R_f$. The method includes combining a perfluorinated anhydride of the formula $R_fC(O)OC(O)R_f$ with hydrogen peroxide and a salt, a metal oxide, a metal hydroxide, a metal alcoholate, or a combination thereof.

In still another embodiment, there is provided a method of making a composition that includes a perfluorinated peroxide of the formula $R_fC(O)OOC(O)R_f$. The method includes combining a perfluorinated anhydride of the formula $R_fC(O)OC(O)R_f$ with a perfluorinated peracid, a perfluorinated acid, and a salt, a metal oxide, a metal hydroxide, a metal alcoholate, or a combination thereof, to form the composition that includes the perfluorinated peroxide of the formula $R_fC(O)OOC(O)R_f$, wherein each $R_f$ group is independently a perfluorinated aromatic or aliphatic group, or combinations thereof, optionally including oxygen atoms.

In the formulas listed above, each $R_f$ group is independently a perfluorinated aromatic or aliphatic group, or combinations thereof, optionally including oxygen atoms.

The present invention also provides methods of fluorinating an organic compound (e.g., perfluoroalkylating or perfluoroarylating). The method includes: combining a perfluorinated anhydride of the formula $R_fC(O)OC(O)R_f$ with hydrogen peroxide and a catalytic amount of a salt to form a composition that includes a perfluorinated peroxide of the formula $R_fC(O)OOC(O)R_f$, wherein each $R_f$ group is independently a perfluorinated aromatic or aliphatic group, or combinations thereof, optionally including oxygen atoms; and combining the composition that includes the perfluorinated peroxide with an organic compound to fluorinate the organic compound.

In an alternative embodiment, the present invention provides a method of fluorinating an organic compound that includes: combining a composition that includes a mixture of a perfluorinated peroxide in a perfluorinated acid with an organic compound to fluorinate the organic compound.

In yet another embodiment, the present invention provides a method of fluorinating an organic compound that includes: combining a perfluorinated anhydride of the formula $R_fC(O)OC(O)R_f$ with a perfluorinated peracid, a perfluorinated acid, and a salt, a metal oxide, a metal hydroxide, a metal alcoholate, or a combination thereof, to form the composition that includes the perfluorinated peroxide of the formula $R_fC(O)OOC(O)R_f$, wherein each $R_f$ group is independently a perfluorinated aromatic or aliphatic group, or combinations thereof, optionally including oxygen atoms; and combining the composition that includes the perfluorinated peroxide with an organic compound to fluorinate the organic compound.

The present invention also provides a peroxide of the formula $RC(O)OOC(O)R_f$, wherein the R group is a non-perfluorinated aromatic or aliphatic group, or combinations thereof, optionally including oxygen atoms, and the $R_f$ group is a perfluorinated aromatic or aliphatic group, or combinations thereof, optionally including oxygen atoms, wherein the R and $R_f$ groups each independently have 1–20 carbon atoms, at least one of which has at least 2 carbon atoms. Methods of making such compounds are also included. For example, one method includes: combining a carboxylic acid of the formula $RC(O)OH$ with a perfluorocarboxylic peracid of the formula $R_fC(O)OOH$ in the presence of a perfluorocarboxylic anhydride of the formula $R_fC(O)OC(O)R_f$. In another method, a percarboxylic acid of the formula $RC(O)OOH$ is combined with a perfluorocarboxylic anhydride of the formula $R_fC(O)OC(O)R_f$.

DETAILED DESCRIPTION OF PREFERRED EMBODIMENTS

In one aspect, the present invention provides a method of making a composition including a perfluorinated peroxide of the formula R$_f$C(O)OOC(O)R$_f$. The method includes combining a perfluorinated anhydride of the formula R$_f$C(O)OC(O)R$_f$ with hydrogen peroxide and a secondary reagent (preferably a catalyst) to form the composition including the perfluorinated peroxide R$_f$C(O)OOC(O)R$_f$, wherein each R$_f$ group is independently a perfluorinated aromatic or aliphatic group, or combinations thereof, optionally including oxygen atoms. The secondary reagent is a salt, a metal oxide, a metal hydroxide, a metal alcoholate, or a combination thereof. Preferably, the secondary reagent is a salt.

In the perfluorinated peroxide of the formula R$_f$C(O)OOC(O)R$_f$, the R$_f$ groups independently represent a perfluorinated aromatic group, a perfluorinated straight chain, branched, or cyclic aliphatic group, or combinations thereof, and R$_f$ may optionally include oxygen atoms. Preferably each R$_f$ independently represents a perfluorinated aliphatic group optionally including oxygen atoms. More preferably, R$_f$ includes 1 to 20 carbon atoms. Most preferably, R$_f$ represents a perfluorinated aliphatic group having the formula C$_n$F$_{2n+1}$, where n is preferably an integer from 1 to 18, and more preferably 1 to 10. The term "independently" means that the two R$_f$ groups may be the same or different in any one perfluorinated peroxide.

Perfluorinated anhydrides of the formula R$_f$C(O)OC(O)R$_f$ are generally available through methods well known in the art and are commercially available from sources such as Sigma-Aldrich, St. Louis, Mo. For example, R$_f$C(O)OC(O)R$_f$ may be prepared by reacting ketene with perfluorocarboxylic acid as disclosed, for example, in International Publication No. WO 01/17939. The R$_f$ groups are as defined above.

Aqueous hydrogen peroxide is commercially available at up to about 50% by weight from chemical suppliers (e.g., Sigma-Aldrich, St. Louis, Mo.). Higher concentrations of hydrogen peroxide can be obtained if desired. For example, 95% by weight H$_2$O$_2$ can be prepared by a well-known procedure disclosed in Pizey, S. J. Synthetic Reagents; John Wiley & Sons: New York, 1985; Vol.6, p 60. Typically, higher concentrations of hydrogen peroxide are desired to produce higher concentrations of R$_f$C(O)OOC(O)R$_f$. Preferably the hydrogen peroxide is used as an aqueous solution.

Figure 1:
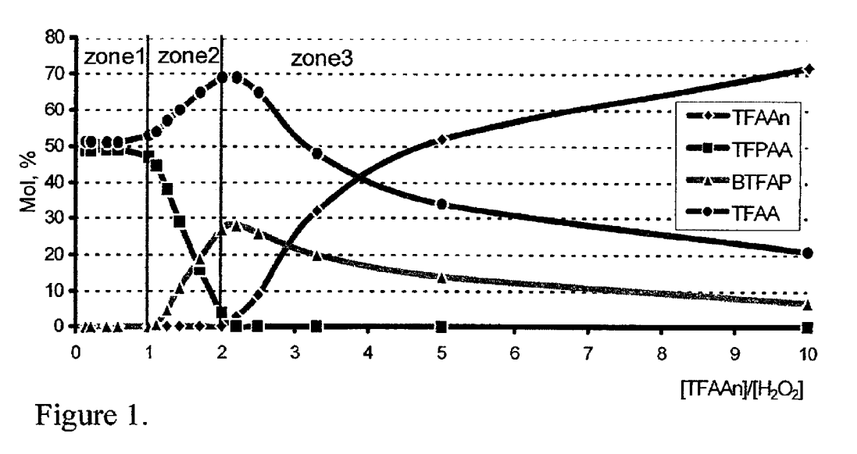
FIG. 1 is a graphical representation of the molar concentration of fluorine containing compounds vs. the ratio of the concentration of trifluoroacetic anhydride [TFAAn] to the concentration of $H_2O_2$ [$H_2O_2$] in the presence of trifluoroacetate anion, as observed by $^{19}F$ nuclear magnetic resonance (NMR) analysis. When the ratio of [TFAAn]/[$H_2O_2$] is less than or equal to about 1 (e.g., Zone 1), approximately equivalent amounts of trifluoroperacetic acid (TFPAA, ■, δ=−74.0) and trifluoroacetic acid (TFAA, ♦, δ=−77.4) are observed. At a [TFAAn]/[$H_2O_2$] ratio of greater than or equal to about 2 (e.g., Zone 3), bis(trifluoroacetyl)peroxide (BTFAP, ▲, δ=−72.8), TFAAn (♦, δ=−77.1), and TFAA (●) are all observed, while TFPAA (■) is not observed. Mixtures of TFAA (●), TFPAA (■), and BTFAP (▲) are observed when the [TFAAn]/[H$_2$O$_2$] ratio is greater than about 1 and less than about 2 (e.g., Zone 2).

The molar ratio of perfluorinated anhydride to hydrogen peroxide depends on the concentration of hydrogen peroxide. For example, if 100% hydrogen peroxide is used, a preferred ratio of a perfluorinated anhydride to hydrogen peroxide is 2 to form perfluorinated anhydride in perfluorinated acid. If a solution of hydrogen peroxide in water is used, more perfluorinated anhydride typically is added to get rid of the water and form a solution of perfluorinated peroxide in perfluorinated acid. Based on 100% hydrogen peroxide, if the molar ratio of a perfluorinated anhydride to hydrogen peroxide is less than 2 but more then 1 (see, e.g., FIG. 1), the products are perfluorinated acid, perfluorinated peracid, and perfluorinated peroxide. If the molar ratio of perfluorinated anhydride to hydrogen peroxide is 1 or less than 1, the products are perfluorinated acid, perfluorinated peracid, and hydrogen peroxide. If the molar ratio of perfluorinated anhydride to hydrogen peroxide is more than 2, the products are perfluorinated acid, perfluorinated peroxide, and perfluorinated anhydride. Thus, a preferred range of ratios of perfluorinated anhydride to hydrogen peroxide, based on 100% hydrogen peroxide, is about 1.5 to about 10, and a more preferred range of ratios is about 1.75 to about 3.25.

It is believed that the process of the reaction between a perfluorinated anhydride and hydrogen peroxide can be represented by the following two consecutive reactions, 1 and 2 (although these are not necessarily limiting to the present invention):

1. $H_2O_2 + (C_nF_{2n+1}C(O))_2O = C_nF_{2n+1}C(O)OOH + C_nF_{2n+1}C(O)OH$

Thus, it is also within the scope of the present invention to combine a perfluorinated anhydride of the formula R$_f$C(O)OC(O)R$_f$ with a mixture (preferably a solution) of a perfluorinated peracid (preferably a perfluorocarboxylic peracid of the formula R$_f$C(O)OOH) in a perfluorinated acid (preferably a perfluorocarboxylic acid of the formula R$_f$C(O)OH) in the presence of a salt, metal oxide, metal hydroxide, metal alcoholate, and/or combinations thereof, to obtain the perfluorinated peroxide of the formula R$_f$C(O)OOC(O)R$_f$ (e.g., bis(perfluoroacyl) peroxide). In this embodiment, the R$_f$ groups are as defined above. In this embodiment, the ratios of perfluorinated anhydride to perfluorinated peracid (and perfluorinated acid) are from 0.1:1 to 100:1, and more preferably about 1:1. A solution of a perfluorocarboxylic peracid in a corresponding perfluorinated acid can be prepared by a well-known procedure described, for example, in P. A. Krasutsky et al., *J. Org. Chem.*, 2000, 65, 3926. A preferred solution includes a concentration of perfluorocarboxylic peracid in perfluorinated carboxylic acid of about 0.0001% by weight (i.e., wt-%)) to about 100% by weight.

In some embodiments of the invention, a catalytic amount a salt, a metal oxide, a metal hydroxide, a metal alcoholate, or a combination thereof is combined with the perfluorinated anhydride and the hydrogen peroxide (or the perfluorinated anhydride, perfluorinated peracid, and perfluorinated acid). A catalytic amount, as used herein, is less than 2.5 mole %, preferably at most about 1 mole %, more preferably at most about 0.5 mole %, and most preferably at most about 0.1 mole %, based on moles of hydrogen peroxide. A catalytic amount, as used herein, is preferably at least about 0.0001 mole %, more preferably at least about 0.001 mole %, and most preferably at least about 0.01 mole %, based on moles of hydrogen peroxide.

Alternatively, a catalytic amount, as used herein, is less than 5 mole %, preferably at most about 2.5 mole %, more preferably at most about 1 mole %, and most preferably at most about 0.5 mole %, based on moles of perfluorinated anhydride. A catalytic amount, as used herein, is preferably at least about 0.001 mole %, more preferably at least about 0.005 mole %, and most preferably at least about 0.01 mole %, based on moles of perfluorinated anhydride.

In contrast, in the preparation of bis(trifluoroacetyl) peroxide, Japanese Patent Application No. 1-249752

(Sawada et al.) discloses the use of 2.5 to 6000 mole % of sodium and/or potassium carbonate, based on moles of hydrogen peroxide, and 5 to 300 mole % of sodium and/or potassium carbonate, based on moles of trifluoroacetic anhydride.

Salts useful in the present invention include both inorganic and organic salts. Preferably, the salt includes, for example, a Group IA (e.g., Li, Na, etc.), a Group IIA (Be, Mg, etc.), or a Group IIIA (e.g., Al, Ga, etc.) cation (e.g., currently referred to as Groups 1, 2, and 13 of the Periodic Table). More preferred cations include, for example, lithium, sodium, potassium, calcium, barium, cesium, strontium, magnesium, aluminum, or combinations thereof. Useful salts may include an organic and/or inorganic anion. Preferably, the salt is a source of a basic anion. Preferred inorganic anions include, for example, sulfate, nitrate, halide, phosphate, silicate, borate, or combinations thereof. Preferred organic ions include, for example, carboxylates (e.g., carboxylates, perfluorocarboxylates). Preferably the carboxylate is an acetate (e.g., acetate, trifluoroacetate), a propionate, a butyrate, an iso-butyrate, or combinations thereof. The carboxylate can be a salt of a saturated fatty acid if desired. In some embodiments of the present invention, the salt is a non-carbonate salt (i.e., the salt does not include carbonate anions).

Metal oxides useful in the present invention have the formula $M_xO_y$, wherein M is a metal, x=1 to 2, and y=1 to 3. Preferred metals (M) include those in Groups IA, IIA, and IIIA (current Groups 1, 2, and 13) of the Periodic Table. More preferred metals include, for example, lithium, sodium, potassium, calcium, barium, cesium, strontium, magnesium, aluminum, or combinations thereof. Preferred metal oxides include, for example, lithium oxide, sodium oxide, potassium oxide, or combinations thereof.

Metal hydroxides useful in the present invention preferably have the formula $M(OH)_z$, wherein M is a metal and z=1 to 3. Preferred metals (M) include those in Groups IA, IIA, and IIIA (current Groups 1, 2, and 13) of the Periodic Table. More preferred metals include, for example, lithium, sodium, potassium, calcium, barium, cesium, strontium, magnesium, aluminum, or combinations thereof. Preferred metal hydroxides include, for example, lithium hydroxide, sodium hydroxide, potassium hydroxide, or combinations thereof.

Metal alcoholates useful in the present invention have the formula $M(OR)_x$, wherein M is a metal and x=1 to 3. Preferred metals (M) include those in Groups IA, IIA, and IIIA (current Groups 1, 2, and 13) of the Periodic Table. More preferred metals include, for example, lithium, sodium, potassium, calcium, barium, cesium, strontium, magnesium, aluminum, or combinations thereof. Preferred metal alcoholates include, for example, lithium methylate, lithium ethylate, lithium isopropylate, sodium methylate, sodium ethylate, sodium isopropylate, potassium methylate, potassium ethylate, potassium isopropylate, or combinations thereof.

Although not wishing to be bound by theory, it is believed that the salt, metal oxide, metal hydroxide, metal alcoholate, and/or combinations thereof may function as efficient basic catalysts because of the higher nucleophilicity of perfluorocarboxylate ion ($R_fC(O)O^-$) compared to the corresponding perfluorocarboxylic acid. Rapid ion exchange in perfluorocarboxylic acid may also facilitate the catalytic activity.

When the perfluorinated anhydride, the hydrogen peroxide, and the salt, metal oxide, metal hydroxide, metal alcoholate, or combination thereof are combined, they preferably form a single phase system. As used herein, a single phase system means that there are no perceptible phase separation lines.

The reactions described above can be carried out within a wide range of temperatures as desired. Preferably, the temperature is at most about 40° C., more preferably at most about 30° C. Preferably, the temperature is at least about −45° C., more preferably at least about −20° C., and most preferably at least about 20° C. The reaction may be run in air or under an inert atmosphere (e.g., nitrogen or argon).

It is preferable that air and moisture be excluded from the composition including the perfluorinated peroxide if the composition is to be stored for extended periods of time. Organic solvents can be added to the composition to adjust the concentration of the perfluorinated peroxide as desired, but typically the reaction mixture and resultant product composition are substantially free of organic solvents. If used, inert organic solvents, such as freons or solvents of the formula $C_xF_nCl_mH_y$, where x=1–10, n=0–24, m=0–24, y=0–12, are preferred.

Preferably, the perfluorinated peroxide is formed in a yield of at least about 80%, more preferably at least about 90%, even more preferably at least about 98%, and most preferably at least about 100%, based on the amount of active oxygen. As used herein, the amount of "active oxygen" refers to the moles of hydrogen peroxide (or moles of perfluorinated peracid (e.g., perfluorcarboxylic peracid) for embodiments in which hydrogen peroxide is not used).

In some embodiments of the present invention, the composition including the perfluorinated peroxide may be formed as a non-aqueous composition.

As stated above, the composition including the perfluorinated peroxide may also include a perfluorinated acid, preferably trifluoroacetic acid. The perfluorinated acid can be removed before the composition is used, or the composition can be used as produced. The composition including the perfluorinated peroxide and the perfluorinated acid may have improved stability over other compositions including perfluorinated peroxides. For example, bis(trifluoroacetic) peroxide (BTFAP) manifests high stability in trifluoroacetic acid (TFAA). As evidence of this, the concentration of a 28% solution of BTFAP in TFAA remained essentially unchanged (26.5%) at −10° C. for 6 months. It is known, that the stability of other bis(perfluoroacyl) peroxides might be lower, but they are also sufficiently stable for industrial/ laboratory safe operations when maintained at −10° C. in the corresponding perfluorinated acid.

Perfluorinated peroxides are useful, for example, for fluorinating organic compounds with $R_f$ groups as defined above (e.g., perfluoroalkylate, perfluoroarylate). For example, a composition including a perfluoroalkyl peroxide may be combined with an organic compound to perfluoroalkylate the organic compound. Preferred methods involve perfluorinating the organic compound. When the organic compound is a polymerizable organic compound, the fluorination may initiate a polymerization reaction of the organic compound. Other methods in which bis(perfluoroacyl) peroxides, for example, are useful include methods described in H. Sawada, *Chem. Rev.*, 1996, 96, 1779–1808.

In another aspect, the present invention provides a peroxide of the formula $RC(O)OOC(O)R_f$. $R_f$ represents a perfluorinated aromatic group, a perfluorinated straight chain, branched, or cyclic aliphatic group, or combinations thereof, and $R_f$ may optionally include oxygen atoms. Preferably, $R_f$ represents a perfluorinated aliphatic group optionally including oxygen atoms. More preferably, $R_f$ includes 1 (preferably 2, more preferably 3, most preferably 4) to 20 carbon atoms. Most preferably, $R_f$ represents a perfluorinated aliphatic group having the formula $C_nF_{2n+1}$, where n is preferably an integer from 2 to 18, and more preferably 2 to 10. R represents a non-perfluorinated aromatic group, a non-perfluorinated straight chain, branched, or cyclic aliphatic group, or combinations thereof, and R may optionally include oxygen atoms. Preferably, R represents an aliphatic group optionally including oxygen atoms. More preferably, R includes 1 (preferably 2, more preferably 3, most preferably 4) to 20 carbon atoms. Most preferably, R represents an aliphatic group having the formula $C_nH_{2n+1}$, where n is preferably an integer from 2 to 18, more preferably 2 to 10. For certain embodiments, at least one of the R and $R_f$ groups each independently have 2–10 carbon atoms, and more preferably 2–5 carbon atoms. Such compounds are believed to be generally less stable than compounds in which the R and $R_f$ groups have only one carbon atom each. This is advantageous for many synthetic procedures, such as carboxylation, for example.

Peroxides of the formula $RC(O)OOC(O)R_f$ can be synthesized by the reaction of a carboxylic acid of the formula RC(O)OH with a perfluorocarboxylic peracid of the formula $R_fC(O)OOH$ in the presence of a perfluorocarboxylic anhydride of the formula $R_fC(O)OC(O)R_f$. The perfluorocarboxylic peracid could be used as a solution in a corresponding perfluorinated acid. A useful temperature range for the preparation of these compounds is about −50° C. to about +30° C. (depending on the stability of the perfluorinated peroxides). The molar ratio of the carboxylic acid to the perfluorocarboxylic anhydride is preferably about 1:1 to about 1:20, and more preferably about 1:6. The molar ratio of the carboxylic acid to the perfluorocarboxylic peracid is preferably about 1:0.5 to about 1:10, and more preferably about 1:1. A solution of a perfluorocarboxylic peracid in a corresponding perfluorinated acid can be prepared by a well-known procedure described, for example, in P. A. Krasutsky et al., *J. Org. Chem.*, 2000, 65, 3926. A preferred solution includes a concentration of perfluorocarboxylic peracid in perfluorinated carboxylic acid of about 0.0001% by weight (i.e., wt-%)) to about 100% by weight.

Peroxides of the formula $RC(O)OOC(O)R_f$ can also be synthesized by the reaction of a percarboxylic acid of the formula RC(O)OOH with a perfluorocarboxylic anhydride of the formula $R_fC(O)OC(O)R_f$. A useful temperature range for the preparation of these compounds is about −50° C. to about +30° C. (depending on the stability of the perfluorinated peroxides). The molar ratio of the percarboxylic acid to the perfluorocarboxylic anhydride is preferably about 1:1 to about 1:100, and more preferably about 1:20. It is possible to use an inert organic solvent such as freons or solvents of the formula $C_xF_nCl_mH_y$, where x=1–10, n=0–24, m=0–24, y=0–12, in such preparation methods. Percarboxylic acids of the formula RC(O)OOH can be prepared by a well-known literature procedure described, for example, in D. Swern, *Org. Peroxides*, 1970, 1, 475–516 and could be used as a solution in an inert organic solvent.

The present invention is illustrated by the following examples. It is to be understood that the particular examples, materials, amounts, and procedures are to be interpreted broadly in accordance with the scope and spirit of the invention as set forth herein.

EXAMPLES

All materials were commercially available and used as received unless otherwise specified. Trifluoroacetic anhydride, pentafluoropropionic anhydride, heptafluorobutyric anhydride, and nonafluorovaleric anhydride were purchased from Sigma-Aldrich, St. Louis, Mo. and used freshly distilled. Aqueous hydrogen peroxide is commercially available at up to about 50% by weight from chemical suppliers (e.g., Sigma-Aldrich, St. Louis, Mo.). Ninety-five percent (95%) by weight $H_2O_2$ was prepared by the well-known literature procedure described in Pizey, S. J. Synthetic Reagents; John Wiley & Sons: New York, 1985; Vol.6, p 60. The salts used are available from Sigma-Aldrich, St. Louis, Mo.

$^{19}F$ nuclear magnetic resonance (NMR) analysis was carried out on a Varian Unity Inova 300 MHz spectrometer at 282.2 MHz, with chemical shifts δ relative to $CFCl_3$ external standard (negative chemical shifts being upfield).

Example 1

The general procedure used for preparing the solutions of bis(perfluoroacyl) peroxides in the corresponding perfluorocarboxylic acid was as follows: $H_2O_2$ (95%, 1.61 g, 45.0 mmol $H_2O_2$) was added dropwise into a well-stirred solution of potassium perfluorocarboxylate (0.045 mmol) in freshly distilled bis(perfluoroacyl) anhydride (100 mmol) at 0° C. A 31% (mol) solution of bis(perfluoroacyl) peroxide in the perfluoroacyl acid was obtained.

$H_2O_2$ (>95%) was combined with freshly distilled trifluoroacetic anhydride (TFAAn) at concentration ratios of [TFAAn]/[$H_2O_2$] of about 1 to about 10 at room temperature. The composition of each sample was analyzed by $^{19}F$ NMR. Stoichiometric formation of trifluoroperacetic acid (TFPAA, δ=−74.0), trifluoroacetic acid (TFAA, δ=−77.4), and non-reacted trifluoroacetic anhydride (TFAAn, δ=−77.1) was observed when the ratio [TFAAn]/[$H_2O_2$] was greater than about 1. When the ratio [TFAAn]/[$H_2O_2$] was greater than about 5, only traces of bis(trifluoroacetyl) peroxide (BTFAP, δ=−72.8) appeared in the reaction mixture.

Acidic catalysts ($H_2SO_4$, $BF_3$) did not change the ratio of components. However, the addition of trace amounts of sodium or potassium salts of TFAA (less than 0.1% (molar) of the concentration of $H_2O_2$), dramatically changed the product distribution as graphically illustrated in FIG. 1. When the ratio of [TFAAn]/[$H_2O_2$] was less than or equal to about 1 (e.g., Zone 1), an equivalent amount of trifluoroperacetic acid (TFPAA, ■, δ=−74.0) and trifluoroacetic acid (TFAA, ●, δ=−77.4) was observed. The peak for TFPAA (■) completely disappeared and the peak for bis(trifluoroacetyl)peroxide (BTFAP, ▲, δ=−72.8) appeared when the ratio of [TFAAn]/[$H_2O_2$] was greater than or equal to about 2 (e.g., Zone 3). When the ratio [TFAAn]/[$H_2O_2$] was greater than about 5, only traces of BTFAP (▲) appeared in the reaction mixture.

Example 2

A solution of bis(trifluoroacetyl) peroxide in trifluoroacetic acid was prepared by addition of $H_2O_2$ (95%, 1.61 g, 45.0 mmol $H_2O_2$) dropwise into a well-stirred solution of potassium trifluoroacetate (6.8 mg, 0.045 mmol) in freshly distilled bis(trifluoroacetic) anhydride (21 g, 100 mmol) at 0° C. A 31% (mol) solution of bis(trifluoroacetyl) peroxide in the trifluoroacetic acid was obtained.

Example 3

In a manner similar to that of Example 1, $H_2O_2$ (>95%) was combined with pentafluoropropionic anhydride to give bis(pentafluoropropanoyl) peroxide (δ−85.1, −121.3) in pentafluoropropionic acid.

Example 4

In a manner similar to that of Example 1, $H_2O_2$ (>95%) was combined with heptafluorobutyric anhydride to give bis(heptafluorobutanoyl) peroxide (δ−82.6, −118.4, −128.2) in heptafluorobutyric acid.

Example 5

In a manner similar to that of Example 1, $H_2O_2$ (>95%) was combined with nonafluorovaleric anhydride to give bis(nonafluoropentanoyl) peroxide (δ−83.2, −117.9, −124.8, −127.5) in nonafluorovaleric acid.

Example 6

It is possible to use a lower concentration of hydrogen peroxide. For example, from a commercially available 30% solution of hydrogen peroxide in water it is possible to produce an 8% (mole) solution of bis(trifluoroacetyl) peroxide (BPFAP) in trifluoroacetic acid. This solution was obtained when 30% $H_2O_2$ (1.77 g, 15.6 mmol $H_2O_2$) was added dropwise into a well-stirred solution of $R_fCOOK$ (6.8 mg, 0.047 mmol) in freshly distilled bis(trifluoroacetyl) anhydride (21 g, 100 mmol) at 0° C. After adding the $H_2O_2$, the reaction mixture was stirred for 10 minutes (min) at 0° C. The concentration of BPFAP was measured by $^{19}F$ NMR spectra.

Example 7

Propionic acid (3 grams (g), 40.5 millimoles (mmol)) was added into a freshly distilled trifluoroacetic anhydride (34 g, 162.1 mmol) and stirred at room temperature for 20 min. A solution of TFPAA in TFAA (11.7 g, 40.5 mmol of TFPAA) was then added dropwise into a well-stirred solution of carboxylic acid in freshly distillated TFAAn at −10° C. and stirred for another 20 min. The concentration of propionyl-trifluoroacetyl peroxide in trifluoroacetic acid/trifluoroacetic anhydride was measured by $^{19}F$ NMR. $^1H$ NMR ($CF_3COOH$, 300 MHz): δ 2.07 (q, J=7.5 Hz, 2H), 0.77 (t, J=7.5 Hz, 3H). $^{13}C$ NMR ($CF_3COOH$, 75 MHz): δ 171.2, 154.7 (q, $^2J_{CF}$=48 Hz), 113.4 (q, $^1J_{CF}$=287.8 Hz), 22.5, 7.1. $^{19}F$ NMR ($CF_3COOH$, 282.2 MHz): δ−73.3.

Example 8

A solution of bis(trifluoroacetyl) peroxide in trifluoroacetic acid was prepared by addition of freshly distilled bis(trifluoroacetic) anhydride (21 g, 100 mmol) dropwise into a well-stirred solution of potassium trifluoroacetate (6.8 mg, 0.045 mmol) in trifluoroperacetic acid (13 g, 100 mmol) and trifluoroacetic acid (15.9 g, 139.5 mmol) at 0° C. A 29.5% (mol) solution of bis(trifluoroacetyl) peroxide in the trifluoroacetic acid was obtained.

The complete disclosure of all patents, patent applications, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of making an acidic composition comprising a perfluorinated peroxide of the formula $R_fC(O)OOC(O)R_f$, the method comprising combining (a) a perfluorinated anhydride of the formula $R_fC(O)OC(O)R_f$ with (b) hydrogen peroxide and a catalytic amount of (c) a Group 1, 2, or 13 metal oxide, a Group 1, 2, or 13 metal hydroxide, a Group 1, 2, or 13 metal alcoholate, or a combination thereof, to form the acidic composition comprising the perfluorinated peroxide of the formula $R_fC(O)OOC(O)R_f$, wherein each $R_f$ group is independently a perfluorinated aromatic or aliphatic group, or combinations thereof, optionally including oxygen atoms, and a perfluorinated acid formed in situ;

with the proviso that the method does not comprise combining a metal peroxide with (a), (b), or (c), or forming a metal peroxide in situ.

2. The method of claim 1 wherein (a) the perfluorinated anhydride, (b) the hydrogen peroxide, and (c) the Group 1, 2, or 13 metal oxide, Group 1, 2, or 13 metal hydroxide, Group 1, 2, or 13 metal alcoholate, or combination thereof form a single phase system.

3. The method of claim 1 wherein the perfluorinated peroxide is formed in a yield of at least about 80% based on the amount of active oxygen.

4. The method of claim 3 wherein the perfluorinated peroxide is formed in a yield of at least about 90% based on the amount of active oxygen.

5. The method of claim 1 wherein the hydrogen peroxide is added as an aqueous solution.

6. The method of claim 1 wherein the perfluorinated acid is trifluoroacetic acid.

7. The method of claim 1 wherein each $R_f$ group is independently a perfluorinated aliphatic group optionally including oxygen atoms.

8. The method of claim 7 wherein each $R_f$ group is independently a $C_nF_{2n+1}$ group, wherein n is 1–10.

9. The method of claim 1 wherein (a) the perfluorinated anhydride, (b) the hydrogen peroxide, and (c) the Group 1, 2, or 13 metal oxide, Group 1, 2, or 13 metal hydroxide, Group 1, 2, or 13 metal alcoholate, or combination thereof are combined at a temperature of about −45° C. to about 40° C.

10. A method of making an acidic composition comprising a perfluorinated peroxide of the formula $R_fC(O)OOC(O)R_f$, the method comprising combining (a) a perfluorinated anhydride of the formula $R_fC(O)OC(O)R_f$ with (b) hydrogen peroxide and a catalytic amount of (c) a metal oxide, a metal hydroxide, a metal alcoholate, or a combination thereof, to form the acidic composition comprising the perfluorinated peroxide of the formula $R_fC(O)OOC(O)R_f$, wherein each $R_f$ group is independently a perfluorinated aromatic or aliphatic group, or combinations thereof, optionally including oxygen atoms, and a perfluorinated acid formed in situ;

wherein the metal is selected from the group consisting of lithium, sodium, potassium, calcium, barium, cesium, strontium, magnesium, aluminum, and combinations thereof; and with the proviso that the method does not comprise combining a metal peroxide with (a), (b), or (c), or forming a metal peroxide in situ.

11. A method of making a non-aqueous composition comprising a perfluorinated peroxide of the formula $R_fC(O)OOC(O)R_f$, the method comprising combining (a) a perfluorinated anhydride of the formula $R_fC(O)OC(O)R_f$ with (b) hydrogen peroxide and, a catalytic amount of (c) a Group 1, 2, or 13 metal oxide, a Group 1, 2, or 13 metal hydroxide, a Group 1, 2, or 13 metal alcoholate, or a combination thereof, to form the non-aqueous composition comprising the perfluorinated peroxide of the formula $R_fC(O)OOC(O)R_f$, wherein each $R_f$ group is independently a perfluorinated aromatic or aliphatic group, or combinations thereof, optionally including oxygen atoms.

12. A method of making an acidic composition comprising a perfluorinated peroxide of the formula $R_fC(O)OOC$ (O)R$_f$, the method comprising combining (a) a perfluorinated anhydride of the formula R$_f$C(O)OC(O)R$_f$ with (b) a perfluorinated peracid, (c) a perfluorinated acid, and a catalytic amount of (d) a Group 1, 2, or 13 metal oxide, a Group 1, 2, or 13 metal hydroxide, a Group 1, 2, or 13 metal alcoholate, or a combination thereof, to form the acidic composition comprising the perfluorinated peroxide of the formula R$_f$C(O)OOC(O)R$_f$, wherein each R$_f$ group is independently a perfluorinated aromatic or aliphatic group, or combinations thereof, optionally including oxygen atoms, with the proviso that the method does not comprise combining a metal peroxide with (a), (b), (c), or (d), or forming a metal peroxide in situ.

13. A method of making an acidic composition comprising a perfluorinated peroxide of the formula R$_f$C(O)OOC(O)R$_f$, the method comprising combining (a) a perfluorinated anhydride of the formula R$_f$C(O)OC(O)R$_f$ with (b) hydrogen peroxide and a catalytic amount of (c) a Group 1, 2, or 13 metal oxide, a Group 1, 2, or 13 metal hydroxide, a Group 1, 2, or 13 metal alcoholate, or a combination thereof, to form the acidic composition comprising the perfluorinated peroxide of the formula R$_f$C(O)OOC(O)R$_f$, wherein each R$_f$ group is independently a perfluorinated aromatic or aliphatic group, or combinations thereof, optionally including oxygen atoms, and a perfluorinated acid formed in situ.

14. The method of claim 13 wherein (a) the perfluorinated anhydride, (b) the hydrogen peroxide, and (c) the Group 1, 2, or 13 metal oxide, Group 1, 2, or 13 metal hydroxide, Group 1, 2, or 13 metal alcoholate, or combination thereof form a single phase system.

15. The method of claim 13 wherein the perfluorinated peroxide is formed in a yield of at least about 80% based on the amount of active oxygen.

16. The method of claim 15 wherein the perfluorinated peroxide is formed in a yield of at least about 90% based on the amount of active oxygen.

17. The method of claim 13 wherein the hydrogen peroxide is added as an aqueous solution.

18. The method of claim 13 wherein the perfluorinated acid is trifluoroacetic acid.

19. The method of claim 13 wherein each R$_f$ group is independently a perfluorinated aliphatic group optionally including oxygen atoms.

20. The method of claim 19 wherein each R$_f$ group is independently a C$_n$F$_{2n+1}$ group, wherein n is 1–10.

21. The method of claim 13 wherein (a) the perfluorinated anhydride, (b) the hydrogen peroxide, and (c) the Group 1, 2, or 13 metal oxide, Group 1, 2, or 13 metal hydroxide, Group 1, 2, or 13 metal alcoholate, or combination thereof are combined at a temperature of about −45° C. to about 40° C.

22. A method of making an acidic composition comprising a perfluorinated peroxide of the formula R$_f$C(O)OOC(O)R$_f$, the method comprising combining (a) a perfluorinated anhydride of the formula R$_f$C(O)OC(O)R$_f$ with (b) hydrogen peroxide and a catalytic amount of (c) a metal oxide, a metal hydroxide, a metal alcoholate, or a combination thereof, to form the acidic composition comprising the perfluorinated peroxide of the formula R$_f$C(O)OOC(O)R$_f$, wherein each R$_f$ group is independently a perfluorinated aromatic or aliphatic group, or combinations thereof, optionally including oxygen atoms, and a perfluorinated acid formed in situ;

wherein the metal is selected from the group consisting of lithium, sodium, potassium, calcium, barium, cesium, strontium, magnesium, aluminum, and combinations thereof.

23. A method of making an acidic composition comprising a perfluorinated peroxide of the formula R$_f$C(O)OOC(O)R$_f$, the method comprising combining (a) a perfluorinated anhydride of the formula R$_f$C(O)OC(O)R$_f$ with (b) a perfluorinated peracid, (c) a perfluorinated acid, and a catalytic amount of (d) a Group 1, 2, or 13 metal oxide, a Group 1, 2, or 13 metal hydroxide, a Group 1, 2, or 13 metal alcoholate, or a combination thereof, to form the acidic composition comprising the perfluorinated peroxide of the formula R$_f$C(O)OOC(O)R$_f$, wherein each R$_f$ group is independently a perfluorinated aromatic or aliphatic group, or combinations thereof, optionally including oxygen atoms.

* * * * *

UNITED STATES PATENT AND TRADEMARK OFFICE
CERTIFICATE OF CORRECTION

PATENT NO. : 6,911,561 B2
DATED : June 28, 2005
INVENTOR(S) : Krasutsky et al.

It is certified that error appears in the above-identified patent and that said Letters Patent is hereby corrected as shown below:

Title page,
Item [56], References Cited, OTHER PUBLICATIONS,
"Kratsutsky" 2nd reference, please delete "Event-" and insert -- Event --; and please delete "& session" and insert -- &session --.
"Kratsutsky" 4th reference, please delete "192089 &session" and insert
-- 192089&session --;
"Zhao et al." reference, please delete "Perfluoro-" and insert -- Perfluoro- and --;

Column 1,
Line 23, please insert the following lines after "conditions." and before "This"
-- $R_fC(O)X+aq.Na_2O_2(2NaOH)+H_2O_2)-R_fC(O)OOC(O)R_f$
  $CF_3C(O)OC(O)CF_3+aq.BaO_2-CF_3C(O)OOC(O)CF_3$
  $CF_3C(O)OC(O)CF_3+aq.Na_2O_2-CF_3C(O)OOC(O)CF_3$ --;

Column 10,
Line 58, please delete "$R_f(C(O)OC(O)R_f$" and insert -- $R_fC(O)OC(O)R_f$ --;

Column 11,
Line 17, please delete "$R_f(O)OC(O)R_f$" and insert -- $R_fC(O)OC(O)R_f$ --.

Signed and Sealed this

Eighth Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,911,561 B2  Page 1 of 1
APPLICATION NO. : 10/163840
DATED : Jume 28, 2005
INVENTOR(S) : Krasutsky et al.

It is certified that error appears in the above-identified patent and that said Letters Patent is hereby corrected as shown below:

Column 1,
Line 23, please insert the following lines after "conditions." and before "This"

$$-- R_fC(O)X + aq.\ Na_2O_2\ (2NaOH + H_2O_2) \rightarrow R_fC(O)OOC(O)R_f$$
$$CF_3C(O)OC(O)CF_3 + aq.\ BaO_2 \rightarrow CF_3C(O)OOC(O)CF_3$$
$$CF_3C(O)OC(O)CF_3 + aq.\ Na_2O_2 \rightarrow CF_3C(O)OOC(O)CF_3 --.$$

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

PATENT NO.       : 6,911,561 B2
APPLICATION NO.  : 10/163840
DATED            : June 28, 2005
INVENTOR(S)      : Krasutsky et al.

It is certified that error appears in the above-identified patent and that said Letters Patent is hereby corrected as shown below:

Column 1,
Line 23, please insert the following lines after "conditions." and before "This"

-- $R_fC(O)X + aq.\ Na_2O_2\ (2NaOH + H_2O_2) \rightarrow R_fC(O)OOC(O)R_f$ $CF_3C(O)OC(O)CF_3 + aq.\ BaO_2 \rightarrow CF_3C(O)OOC(O)CF_3$ $CF_3C(O)OC(O)CF_3 + aq.\ Na_2O_2 \rightarrow CF_3C(O)OOC(O)CF_3$ --.

This certificate supersedes Certificate of Correction issued September 5, 2006.

Signed and Sealed this

Seventh Day of November, 2006

JON W. DUDAS
*Director of the United States Patent and Trademark Office*